United States Patent [19]
Motomura et al.

[11] 4,050,919
[45] Sept. 27, 1977

[54] PROCESS FOR DEVELOPING SEEDLESS FLESHY BERRY OF GRAPES

[75] Inventors: Yoshie Motomura, Sendai; Jiro Ishiyama, Noda, both of Japan

[73] Assignee: Kikkoman Shoyu Co., Ltd., Noda, Japan

[21] Appl. No.: 674,078

[22] Filed: Apr. 6, 1976

[30] Foreign Application Priority Data

Apr. 8, 1975    Japan .................................. 50-41876

[51] Int. Cl.² .......................... A01N 9/36; A01N 9/12
[52] U.S. Cl. ............................................. 71/86; 71/89
[58] Field of Search ....................................... 71/89, 86

[56] References Cited

U.S. PATENT DOCUMENTS 2,993,048  7/1961  Shive et al. .......................... 71/89 X
3,118,753  1/1964  Shive et al. .......................... 71/89 X

FOREIGN PATENT DOCUMENTS 634,472  1/1962  Canada ................................. 71/89

OTHER PUBLICATIONS

The Merck Index, 8th Ed., 1968, p. 21.

Primary Examiner—Joseph Paul Brust
Attorney, Agent, or Firm—Schuyler, Birch, Swindler, McKie & Beckett

[57] ABSTRACT

A composition for use in the treatment for developing seedless fleshy berry of grapes. By treating the flower bunches of a grape tree with a composition containing gibberellin and cyclic 3',5'-adenylic acid in the form of an aqueous solution, it became possible to make seedless fleshy berry from grape trees belonging to varieties other than Delaware, namely belonging to Campbell-Arley, Berry A, Niagara, Kyoho, etc., from which seedless fleshy berry cannot be made by the conventional treatment with gibberellin.

11 Claims, No Drawings

PROCESS FOR DEVELOPING SEEDLESS FLESHY BERRY OF GRAPES

This invention relates to a composition for use in the treatment for developing seedless fleshy berry of grapes. In particular, it relates to a composition for use in the treatment for developing seedless fleshy berry of grapes containing gibberellin and cyclic 3′,5′-adenylic acid and a process for developing said seedless fleshy berry of grapes.

The process for obtaining seedless fleshy berry of grapes by use of gibberellin (hereinafter referred to as GA) has already been disclosed. However, the process is disadvantageous in that its effectiveness in making grapes seedless is greatly dependent on the variety of grape tree to be treated, so that at the present time its practical application is limited to Delaware variety. In Delaware variety of grape trees, indeed, the process is effective in that the flowering time can be hastened by 3 to 5 day, as compared with untreated case, by dipping flower bunch (the terms "flower bunch" means a bunch of multiple flowers at any stage from the beginning of budding to the finish of flowering, namely the time when all the corollas have fallen) into a GA solution about two weeks before the expected full bloom day (there is a time allowance of several days). If the bunch is again treated with the same GA solution about ten days after full bloom, the harvest time of fruit is hastened by one to two weeks as compared with untreated case, and the fruit bunches thus obtained becomes seedless enough to have a higher commercial value. This is probably attributable to that GA retards the formation of seed and stimulates the growth of fruit. When other varieties of grape plants are treated with the same GA solution, however, the fruits are made seedless but most of them stay at the stage of shot berry (the terms "shot berry" means a small, green, seedless, hard berry resting on the plant without falling nor maturing, of which growth has ceased at the stage of flowering so that the size, or diameter, remains at a value of 5 mm or less), allowing only a small percentage of berries to grow up to the stage of seedless flesh berry. Accordingly, the technique cannot be employed in the practical production. Probably, this is attributable to that, in the varieties other than Delaware, GA retards the formation of seed but it cannot stimulate the flesh of berry.

The present inventors conducted an intensive study with the aim of overcoming the above-mentioned difficulty. As a result, there was obtained a new finding that the seedless and flesh berry number of grape can be remarkably increased by treating flower bunches of grape with a combination of GA and cyclic 3′,5′-adenylic acid (hereinafter referred to as CAMP). Based on the above-mentioned finding, the present invention was accomplished.

Thus, this invention provides a composition containing GA and CAMP for use in the treatment for developing seedless fleshy berry of grapes and a process for developing said seedless fleshy berry of grapes.

This invention will be explained below in more detail.

The varieties of grape to which the composition of this invention can successfully be applied include, for example Campbell-Arley, Berry A, Niagara, Kyoho and the like.

The composition of this invention is used in the form of an aqueous solution.

GA used in this invention may be prepared, for example, by the fermentation method or the like. Alternatively, it may also be a commercial product.

The preferable ratio of GA and CAMP in the composition of this invention is 10 to 300: 1 to 10,000 parts by weight. Though the concentration of GA in the composition in the form of an aqueous solution for use in the treatment of grape flower bunches is preferably in the range of 10 to 300 p.p.m., the most preferable concentration is about 80 to 150 p.p.m.

Preferable examples of CAMP, to be used in combination with GA, include the followings: CAMP itself (namely, free CAMP); alkali metal salts and alkaline earth metal salts of CAMP, such as Na salts, K salts, Li salts, Ca salts and the like of CAMP; 8-substituted derivatives of CAMP, such as 8-Br-CAMP, 8-I-CAMP, 8-methyl-CAMP and the like; 6-substituted derivatives of CAMP, such as 6-benzyl-CAMP, 6-allyl-CAMP and the like; and allyl ester CAMP, such as $N^6,O^{2'}$-(dibutyl ester)-CAMP, $N^6$-(butyl ester)-CAMP and the like. All the above-mentioned compounds may be used either alone or in combination thereof. Said CAMP may be prepared, for example, by the synthetic method, the fermentation method or the like. Alternatively, however, it may also be a commercial product.

The concentration of CAMP in the composition in the form of an aqueous solution for use in the treatment is preferably in the range of 1 to 10,000 p.p.m., and most preferably in the range of 100 to 500 p.p.m.

Flower bunches of grape may be treated with a composition in the form of an aqueous solution containing GA and CAMP. Alternatively, it may also be treated in such a manner, for example, that aqueous solutions of GA and CAMP are prepared separately, flower bunches of grape are treated with one of the solutions, and thereafter it is treated with the other solution.

It is preferable to incorporate a conventional spreader comprising a mixture of polyoxyethylenedodecyl ether and polyoxyethylenealkylaryl ether, such as Aerol OP (manufactured by Toho Chemicals Ind. K.K.), Rabiden (manufactured by Nippon Soda K.K.), Nitten (manufactured by Nissan Nagaku K. K.) or the like, into the composition containing GA and CAMP in an amount of 10 to 300 p.p.m. The composition is preferably put to use after its pH value has been adjusted to a value of 2-7 by use of, for example, HCl, $H_2SO_4$, KOH, NaOH or the like in accordance with the needs.

If the composition is further incorporated with an adenine derivative (for example, 6-benzyl-adenine, 6-allyladenine or the like), the effectiveness of the composition in developing seedless fleshy berry of grapes further increases as compared with the case where only GA and CAMP are used in combination. The preferable ratio of GA, CAMP and said adenine derivative in the composition of this invention is 10-300 : 1-10,000 : 1-10,000 parts by weight. The concentration of said adenine derivative in the composition in the form of an aqueous solution is in the range of 1 to 10,000 p.p.m.

Preferably, flower bunches of grapes are treated with a composition containing GA and CAMP in the form of an aqueous solution by means of dipping or spraying. For example, the bunches may be treated with a composition containing GA and CAMP in the form of an aqueous solution by means of dipping or spraying at an appropriate time prior to the expected full bloom day (usually, 14 to 16 days before the expected full bloom day). Alternatively, they may also be once treated in the same manner as above prior to the expected full bloom day and then again treated similarly at an appropriate time after the full bloom (usually, about 10 days after the full bloom day).

Said dipping treatment is carried out, for example, by placing the composition in the form of an aqueous solution in a cup or the like and dipping a flower bunch into it for a time period of, for example, 3 to 10 seconds. Said spraying treatment is preferably carried out, for example, by placing the composition in the form of a aqueous solution in a spray gun and blowing the composition as a mist against flower bunches in such extent that the flower bunches are evenly wetted with the composition.

When the composition of this invention is practised in the above-mentioned manner, the value of seedless fleshy berry rate (namely, the proportion of seedless fleshy berry number to total berry number per one bunch) can be markedly increased after maturation, as compared with the case of the conventional treatment with GA alone, so that there are obtained excellent bunches of fruits of high commercial value.

The composition of this invention is also applicable, with a very high efficiency, to those grape varieties of which conventional treatment with GA alone has hitherto been impractical because of the low value of seedless fleshy berry rate given by it. Therefore, the composition of this invention is quite useful in the production of seedless fleshy fruits of grapes.

The composition and the process of this invention are further illustrated by the following examples, which are not given by way of limitation thereon.

EXAMPLE 1

A 13 years old grape tree, belonging to Campbell-Arley variety and having uniform branch lengths and uniform bunch stages, was used. The excessive bunches were cut away before the treatment to leave only one flower bunch on each flower-bearing branch (new branch). The flower bunches were treated with a composition in the form of an aqueous solution on a fine day selected from the optimum period for the pre-flowering GA treatment (it was 15 days before the expected full bloom day and the actual full bloom was observed on the 15-16th day after the treatment). There were provided six treatment groups as shown in Table 1, and there were found 15 bunches in each treatment group. One of the compositions in the form of an aqueous solution shown in Table 1 was placed in a beaker, and the bunches were dipped into the composition one after another. Each bunch was shaken several times while it was dipped. The time period of dipping was about 5 seconds per one bunch.

TABLE 1

| | The design of treatment groups |
|---|---|
| No. | Content of composition |
| 1 | No treatment (control) |
| 2 | GA 100 p.p.m. |
| 3 | GA 100 p.p.m. + CAMP (Na salt) 300 p.p.m. |
| 4 | GA 100 p.p.m. + CAMP (Na salt) 3000 p.p.m. |
| 5 | GA 100 p.p.m. + 8-Br-CAMP (Na salt) 300 p.p.m. |
| 6 | GA 100 p.p.m. + 8-Br-CAMP (Na salt) 3000 p.p.m. |

The GA was dissolved into a small quantity of ethanol and then diluted with demineralized water to the desired concentration. The CAMP compounds were given in the crystalline form, which were dissolved into water and then put to use. When GA was to be used in combination with one of the CAMP compounds, the components were separately dissolved into water to give solutions having two times greater concentration than intended, and subsequently and solutions were fixed together just before use in a proportion of 1 : 1 by volume. Further, Aerol, OP, as a spreader, was added to each composition so that its concentration become 100 p.p.m. The compositions used in the individual treatment groups had the following pH values: No. 2, pH 4.04; No. 3, pH 4.69; No. 4, pH 5.30; No. 5, pH 4.54; No. 6, pH 5.18.

Harvest Investigation: The fruits were harvested at the time when the seedless fleshy berries colored in purple but the seeded ones did not yet. That is, fruits of the treated groups were harvested 74 days after the treatment, while those of untreated group were harvested an additional 8 days later than the treated ones.

Each of the fruit bunches thus harvested was investigated on bunch weight, total berry number, seeded fleshy berry number, seedless fleshy berry number and shot berry number (shot berry number is as defined above). The results were as shown in Table 2 in terms of average values per one fruit bunch in individual treatment groups.

Table 2

| | Per one fruit bunch | | | | |
|---|---|---|---|---|---|
| No. | Av. bunch weight (g) | Seeded fleshy berry number | Seedless fleshy berry number | Shot berry number | Total berry number |
| 1 | 111.1 | 34.3 | 0.8 | 7.5 | 42.5 |
| 2 | 26.4 | 0.1 | 16.3 | 122.4 | 138.9 |
| 3 | 64.5 | 0.3 | 44.0 | 135.2 | 179.6 |
| 4 | 45.7 | 0.1 | 29.1 | 118.6 | 147.9 |
| 5 | 36.2 | 0.1 | 28.2 | 142.6 | 170.9 |
| 6 | 38.0 | 0.1 | 26.3 | 121.3 | 147.8 |

Seeded fleshy berry weight, seedless flesh berry weight, shot berry weight and seedless fleshy berry diameter of each bunch were also investigated. The results are shown in Table 3 in terms of average values per one berry.

Table 3

| | Per one berry | | | |
|---|---|---|---|---|
| No. | Seeded fleshy berry weight (g) | Seedless fleshy berry weight (g) | Shot berry weight (g) | Seedless fleshy berry diameter (mm) |
| 1 | 3.10 | 0.31 | 0.025 | 7.8 |
| 2 | 2.10 | 1.11 | 0.026 | 11.3 |
| 3 | 2.62 | 1.15 | 0.029 | 11.1 |
| 4 | 2.80 | 1.24 | 0.024 | 11.8 |
| 5 | 1.10 | 0.92 | 0.022 | 10.5 |
| 6 | 1.50 | 1.10 | 0.024 | 11.6 |

Table 4 illustrates seeded fleshy berry rate, seedless fleshy berry rate, shot berry rate and seedless berry rate which were calculated by dividing seeded fleshy berry number, seedless fleshy berry number, shot berry number and seedless berry number (the sum of seedless fleshy berry number and shot berry number) by total berry number.

Table 4

| No. | Seeded fleshy berry rate (%) | Seedless fleshy berry rate (%) | Shot berry rate (%) | Seedless berry rate (%) |
|---|---|---|---|---|
| 1 | 80.6 | 1.8 | 17.6 | 19.4 |
| 2 | 0.1 | 11.7 | 88.2 | 99.9 |
| 3 | 0.3 | 23.0 | 76.7 | 99.7 |
| 4 | 0.6 | 19.2 | 80.2 | 99.4 |
| 5 | 0.1 | 16.5 | 83.4 | 99.9 |

Table 4-continued

| No. | Seeded fleshy berry rate (%) | Seedless fleshy berry rate (%) | Shot berry rate (%) | Seedless berry rate (%) |
|---|---|---|---|---|
| 6 | 0.1 | 17.8 | 82.1 | 99.9 |

The results of Table 2 through Table 4 demonstrate that the grapes obtained by the treatment according to this invention (namely, Nos. 3-6 in the tables) have remarkably increased seedless fleshy berry numbers and very high seedless fleshy berry rates as compared with those obtained by a treatment with GA alone (namely, No. 2 in the tables).

EXAMPLE 2

Each 15 years old grape tree belonging to Berry A, Kyoho and Delaware, respectively, were used as test sample. The treatments were carried out in the same manner as in Example 1 except that the compositions in the form of an aqueous solution shown in Table 5 were used, respectively. The results obtained are shown in Table 5.

Table 5

| Variety | Content of composition | Per one berry Seeded fleshy berry number | Per one berry Seedless fleshy berry number |
|---|---|---|---|
| Berry A | GA 100 p.p.m. | 5 | 20 |
|  | GA 100 p.p.m. + CAMP (Na salt) 50 p.p.m. | 0 | 40 |
| Kyoho | GA 100 p.p.m. | 5 | 15 |
|  | GA 100 p.p.m. + CAMP (Na salt) 300 p.p.m. | 0 | 31 |
| Delaware | GA 100 p.p.m. | 0 | 52 |
|  | GA 100 p.p.m. + CAMP (Na salt) 70 p.p.m. | 0 | 60 |

What is claimed is:

1. A process for developing seedless, fleshy berry of grapes which comprises contacting the flower bunches of grapes with an effective amount of an aqueous solution containing gibberellin and at least one cyclic 3', 5'-adenylic acid compound selected from the group consisting of cyclic 3', 5'-adenylic acid, alkali metal and alkaline earth metal salts of cyclic 3', 5'-adenylic acid, and derivatives of cyclic 3', 5'-adenylic acid, said gibberellin and cyclic 3', 5'-adenylic acid being present in the concentration of 10 to 300 p.p.m. and 1 to 10,000 p.p.m., respectively, and said derivatives of cyclic 3', 5'-adenylic acid being selected from the group consisting of 6-benzyl-cyclic 3', 5'-adenylic acid, 6-allyl-cyclic 3', 5'-adenylic acid, 8-bromo-cyclic 3', 5'-adenylic acid, 8-iodine-cyclic 3', 5'-adenylic acid, 9-methyl-cyclic 3', 5'-adenylic acid, $N^6$, $O^{2'}$-(dibutyl ester)-cyclic 3', 5'-adenylic acid and $N^6$-(butyl ester)-cyclic 3', 5'-adenylic acid.

2. A process according to claim 1 wherein said cyclic 3', 5'-adenylic acid compound is an alkali metal salt and said alkali metal salt is selected from the group consisting of sodium, potassium and lithium.

3. A process according to claim 2 wherein said cyclic 3', 5'-adenylic acid compound is the sodium salt of cyclic 3', 5'-adenylic acid.

4. A process according to claim 1 wherein said cyclic 3', 5'-adenylic acid compound is an alkaline earth metal salt and said alkaline earth metal is calcium.

5. A process according to claim 1 wherein said cyclic 3', 5'-adenylic acid compound is a derivative of cyclic 3', 5'-adenylic acid selected from the group consisting of 6-benzyl-cyclic 3', 5'-adenylic acid, 6-allyl-cyclic 3', 5'-adenylic acid, 8-bromo-cyclic 3', 5'-adenylic acid, 8-iodine-cyclic 3', 5'-adenylic acid, 8-methyl-cyclic 3', 5'-adenylic acid, $N^6$, $O^{2'}$-(dibutyl ester)-cyclic 3', 5'-adenylic acid and $N^6$-(butyl ester)-cyclic 3', 5'-adenylic acid.

6. A process according to claim 1 wherein said cyclic 3', 5'-adenylic acid compound is cyclic 3', 5'-adenylic acid.

7. A process according to claim 1 wherein in addition to said gibberellin and said cyclic 3', 5'-adenylic acid compound there is included an adenine compound selected from the group consisting of 6-benzyl adenine and 6-allyladenine, said adenine compound being present in the concentration of 1 to 10,000 p.p.m.

8. The process of claim 1 wherein said flower bunches of grapes are contacted with said solution by dipping or spraying.

9. The process of claim 1 wherein said grapes are a variety of grape selected from the group consisting of Campbell-Arley, Berry A, Niagara and Kyoho.

10. A process for developing seedless, fleshy berry of grapes which comprises contacting the flower bunches of grapes with an effecting amount of an aqueous solution of gibberellin and an aqueous solution of at least one cyclic 3', 5'-adenylic acid compound selected from the group consisting of cyclic 3', 5'adenylic acid alkali metal and alkaline earth metal salts of cyclic 3', 5'-adenylic acid, and derivatives of cyclic 3', 5'-adenylic acid, said gibberellin and cyclic 3', 5'-adenylic acid being present in the concentration of 10 to 300 p.p.m. and 1 to 10,000 p.p.m., respectively, and said derivatives of cyclic 3', 5'-adenylic acid being selected from the group consisting of 6-benzyl-cyclic 3', 5'-adenylic acid, 6-allyl-cyclic 3', 5'-adenylic acid, 8-bromo-cyclic 3', 5'- adenylic acid, 8-iodine-cyclic 3', 5'-adenylic acid, 8-methyl-cyclic 3', 5'-adenylic acid, $N^6$, $O^{2'}$-(dibutyl ester)-cyclic 3', 5'-adenylic acid and $N^6$-(butyl ester)-cyclic 3', 5'-adenylic acid.

11. A process as claimed in claim 1 wherein said grapes are of the variety of grape Campbell-Arley, Berry A, Niagara or Kyoho.

* * * * *